(12) United States Patent
Fournier et al.

(10) Patent No.: US 10,814,072 B2
(45) Date of Patent: Oct. 27, 2020

(54) RIGID NEEDLE PROTECTOR, METHOD AND MACHINE FOR ASSEMBLING SUCH A RIGID NEEDLE PROTECTOR

(71) Applicant: APTAR STELMI SAS, Villepinte (FR)

(72) Inventors: Ghislain Fournier, La Rochelle (FR); Mickaël Swal, Chauconin Neufmontiers (FR)

(73) Assignee: APTAR STELMI SAS, Villepinte (FR)

( * ) Notice: Subject to any disclaimer, the term of this patent is extended or adjusted under 35 U.S.C. 154(b) by 493 days.

(21) Appl. No.: 15/328,955

(22) PCT Filed: Jul. 24, 2015

(86) PCT No.: PCT/FR2015/052049
§ 371 (c)(1),
(2) Date: Jan. 25, 2017

(87) PCT Pub. No.: WO2016/016556
PCT Pub. Date: Feb. 4, 2016

(65) Prior Publication Data
US 2017/0224932 A1 Aug. 10, 2017

(30) Foreign Application Priority Data
Jul. 28, 2014 (FR) ...................... 14 57269

(51) Int. Cl.
*A61M 5/32* (2006.01)
*A61M 5/20* (2006.01)
*A61M 25/06* (2006.01)

(52) U.S. Cl.
CPC ............ *A61M 5/3213* (2013.01); *A61M 5/20* (2013.01); *A61M 5/3202* (2013.01);
(Continued)

(58) Field of Classification Search
CPC .............. A61M 5/3202; A61M 5/3204; A61M 5/3213; A61M 25/0637; A61J 1/1412; A61J 1/1425
See application file for complete search history.

(56) References Cited

U.S. PATENT DOCUMENTS 2,799,272 A * 7/1957 Peach ................. A61M 5/3202
604/263
4,720,285 A 1/1988 Pickhard
(Continued)

FOREIGN PATENT DOCUMENTS

EP 1 208 861 A1 5/2002
FR 2 777 787 A1 10/1999
(Continued)

OTHER PUBLICATIONS

International Preliminary Report on Patentability issued from the International Bureau in counterpart International Application No. PCT/FR2015/052049, dated Feb. 9, 2017.
(Continued)

*Primary Examiner* — Laura A Bouchelle
*Assistant Examiner* — Justin L Zamory
(74) *Attorney, Agent, or Firm* — Sughrue Mion, PLLC

(57) ABSTRACT

A rigid needle guard (10) comprising an inner part (11) made of elastomeric material, and a rigid outer body (12) that is fastened to said inner part (11) made of elastomeric material via a folded-in portion (121) of the bottom axial end of said rigid outer body (12), said folded-in portion (121) extending radially inwards from the outer peripheral surface (125) of said rigid outer body (12), the outer surface of said folded-in portion (121) forming, at its axially-bottom and radially-outer edge, a sharp and acute angle relative to the outer peripheral surface (125) of said rigid outer body (12).

10 Claims, 3 Drawing Sheets

(52) U.S. Cl.
CPC ...... *A61M 5/3204* (2013.01); *A61M 25/0637* (2013.01); *A61M 2207/00* (2013.01); *A61M 2207/10* (2013.01)

(56) References Cited

U.S. PATENT DOCUMENTS

| | | | | |
|---|---|---|---|---|
| 5,599,309 A | * | 2/1997 | Marshall | A61M 5/2033 604/117 |
| 2002/0062108 A1 | * | 5/2002 | Courteix | A61M 5/3202 604/198 |

FOREIGN PATENT DOCUMENTS

| | | |
|---|---|---|
| NL | 8 520 389 A | 8/1987 |
| WO | 2013/104736 A1 | 7/2013 |

OTHER PUBLICATIONS

International Search Report for PCT/FR2015/052049 dated Oct. 8, 2015.

* cited by examiner

RIGID NEEDLE PROTECTOR, METHOD AND MACHINE FOR ASSEMBLING SUCH A RIGID NEEDLE PROTECTOR

CROSS REFERENCE TO RELATED APPLICATIONS

This application is a National Stage of International Application No. PCT/FR2015/052049 filed Jul. 24, 2015, claiming priority based on French Patent Application No. 1457269 filed Jul. 28, 2014, the contents of all of which are incorporated herein by reference in their entirety.

The present invention relates to a rigid needle guard, a method of assembling such a rigid needle guard, and an assembly machine for performing such an assembly method.

Rigid needle guards are well known. They are generally formed of an inner part made of elastomeric material, such as rubber or a thermoplastic elastomer (TPE) material, and into which the point of the needle is jabbed so as to be isolated from the atmosphere, and a rigid outer body that is fastened to said inner part made of elastomeric material. The rigid outer body serves, in particular, to reinforce the protection of the user of the syringe against being pricked by the needle, by offering rigid outer additional protection that can be perforated by the needle only with great difficulty. In particular, document EP 1 208 861 describes such a rigid needle guard.

This type of rigid needle guard is also used in autoinjectors, where the autoinjector includes a remover member of the outer-cap type that is mounted on the body of the autoinjector, and that, when it is removed from said body of the autoinjector, co-operates with said rigid needle guard so as to remove it from said needle.

FIG. 1 shows a needle guard 10 that is arranged in a remover member 20, in accordance with the prior art. In FIG. 1, it should be observed that only the rigid outer body 12 of the needle guard 10 is visible, the inner part 11 made of elastomeric material not being shown. FIGS. 2 to 4 show the method of assembling the FIG. 1 needle guard. FIG. 2 shows the inner part 11 made of elastomeric material inserted inside the rigid outer body 12. Typically, the insertion stage takes place in a position that is the opposite way up to the position shown in FIG. 2, with the inner part made of elastomeric material 11 dropping by gravity into the rigid outer body 12. FIGS. 3 and 4 show the bottom axial end 121 of the rigid outer body 12 being folded in, so as to fasten said inner part 11 made of elastomeric material in said rigid outer body 12. The folded-in portion 121, formed during the folding step, extends radially inwards from the outer peripheral surface 125 of said rigid outer body. Typically, the folding step is performed hot by means of a folder head 30. It should be observed, in particular in FIG. 4, that the shapes of the folder cavity 31 of the folder head 30 generate a folded-in portion 121 of rounded outer shape on the rigid outer body 12 of the needle guard 10. The rounded shape of the folder cavity 31 is necessary in order to avoid crushing the bottom axial end 121 of the rigid outer body 12 during folding. Unfortunately, the rounded outer shape of the folded-in portion 121 formed on the bottom axial end of the outer body 12 can present drawbacks when the rigid needle guard 10 is used in an autoinjector. Specifically, the remover member 20 of said autoinjector, which comes to co-operate with said needle guard 10 via said folded-in portion 121, may slide over said folded-in portion 121 because of its rounded shape, thereby preventing said needle guard 10 from being removed by means of said remover member 20.

Documents WO 2013/104736 and NL 8 520 389 describe other prior-art devices.

An object of the present invention is to provide a protective device for protecting a syringe needle that does not have the above-mentioned drawbacks.

In particular, an object of the present invention is to provide a protective device for protecting a syringe needle that co-operates in reliable manner with a remover member of an autoinjector.

Another object of the present invention is to provide an assembly method for assembling a protective device for a syringe needle that is simple and inexpensive to implement.

Another object of the present invention is to provide an assembly machine for assembling a protective device for a syringe needle that makes it possible to implement said assembly method.

The present invention thus provides a rigid needle guard comprising an inner part made of elastomeric material, and a rigid outer body that is fastened to said inner part made of elastomeric material via a folded-in portion of the bottom axial end of said rigid outer body, said folded-in portion extending radially inwards from the outer peripheral surface of said rigid outer body, the outer surface of said folded-in portion forming, at its axially-bottom and radially-outer edge, a sharp and acute angle relative to the outer peripheral surface of said rigid outer body.

Advantageously, said sharp and acute angle is less than 90°.

Advantageously, said inner part made of elastomeric material is made of rubber or made of thermoplastic elastomer material.

The present invention also provides a unit formed of a rigid needle guard and of a remover member that is arranged around said rigid needle guard, said rigid needle guard being made as described above, said remover member including a manual grip zone and a co-operation zone for co-operating with said rigid needle guard, said co-operation zone comprising at least one shoulder that extends radially inwards and that co-operates with said axially-bottom and radially-outer edge of said folded-in portion of said rigid outer body of said rigid needle guard, such that axial movement of said remover member causes axial movement of said rigid needle guard.

The present invention also provides a syringe comprising a reservoir and a needle, said syringe including a rigid needle guard as described above.

The present invention also provides an assembly method for assembling a rigid needle guard as described above, the method comprising the following steps:
  inserting said inner part made of elastomeric material into said rigid outer body;
  folding the bottom axial end of said rigid outer body radially inwards by means of a folder head, so as to form a folded-in portion that fastens said inner part made of elastomeric material in said rigid outer body; and
  deforming said folded-in portion with a shaper head so as to shape, on said axially-bottom and radially-outer edge of said folded-in portion, a sharp and acute angle relative to the outer peripheral surface of said rigid outer body.

Advantageously, said step of folding the bottom axial end of said rigid outer body radially inwards is performed by heat or by ultrasound.

Advantageously, said step of deforming said folded-in portion is performed by heat or by ultrasound.

The present invention also provides an assembly machine for assembling a rigid needle guard as described above, for implementing the method as described above, the machine comprising:

an inserter unit for inserting said inner part made of elastomeric material into said rigid outer body;

a folder head for forming a folded-in portion that extends radially inwards, so as to fasten said inner part made of elastomeric material in said rigid outer body; and a shaper head for deforming the rounded outer surface of said folded-in portion so as to shape, on said axially-bottom and radially-outer edge of said folded-in portion, a sharp and acute angle, preferably less than 90°, relative to the outer peripheral surface of said rigid outer body.

Advantageously, said folder head and/or said shaper head operate by heat or by ultrasound.

These characteristics and advantages and others of the present invention appear more clearly from the following detailed description, given by way of non-limiting example, and with reference to the accompanying drawing, in which.

Figure 1:
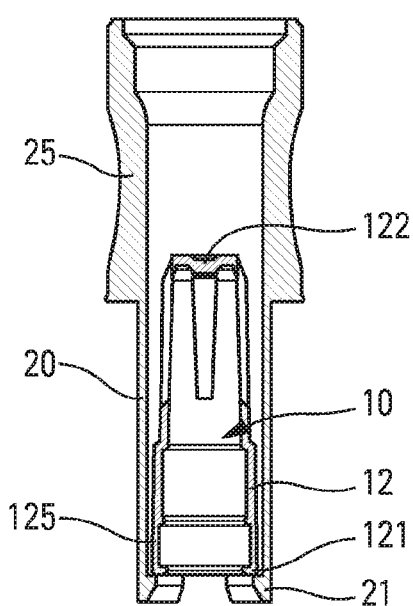
FIG. 1 is a diagrammatic section view of a prior-art rigid needle guard that is arranged in a remover member.
Figure 2:
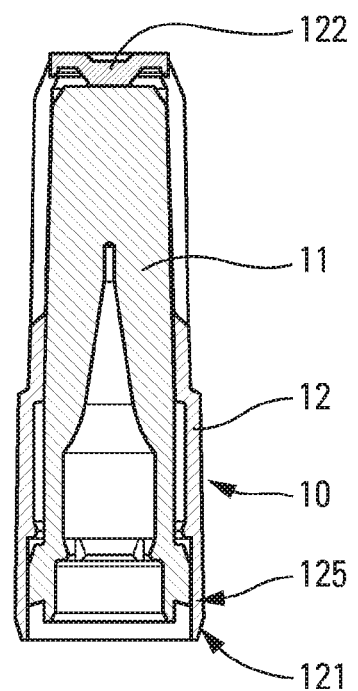
FIG. 2 is a diagrammatic section view of the FIG. 1 rigid needle guard, during assembly, with the inner part made of elastomeric material inserted into the rigid outer body.
Figure 3:
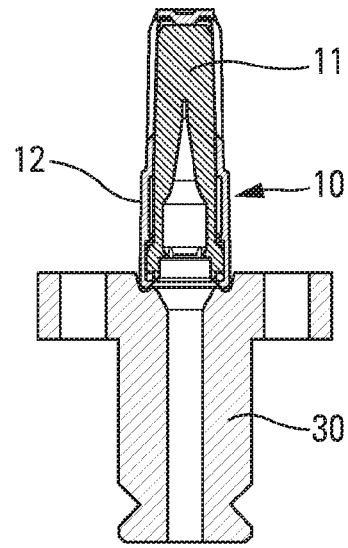
FIG. 3 is a diagrammatic section view of the FIG. 2 rigid needle guard, during assembly, with a folder head deforming the bottom axial end of the rigid outer body, so as to fasten said inner part made of elastomeric material.
Figure 4:
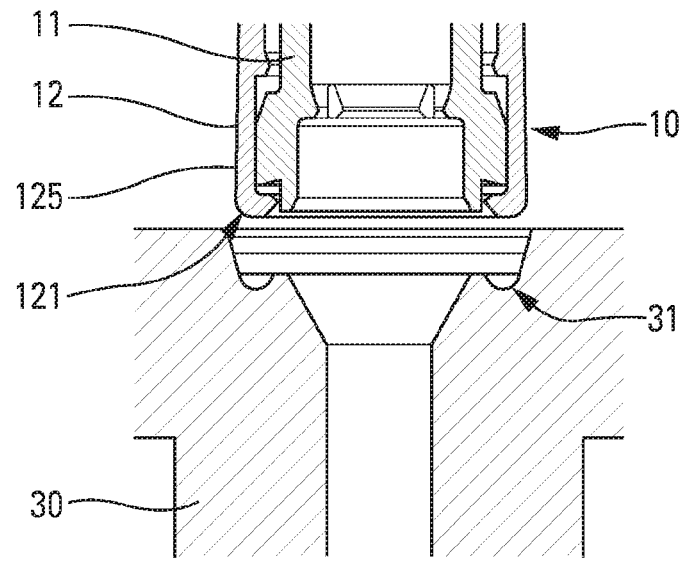
FIG. 4 is a view of a detail showing the shape of the folder head and the shape of the folded-in portion made by the folder head.
Figure 5:
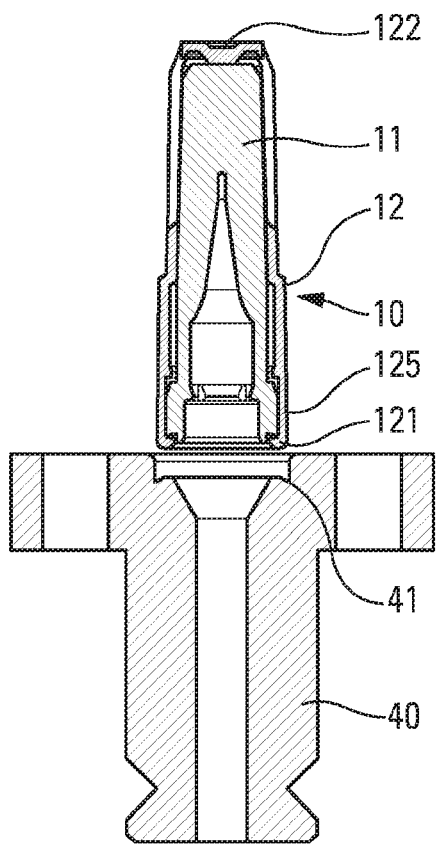
FIG. 5 is a view similar to the view in FIG. 3, showing an advantageous embodiment of the present invention, before actuating a shaper head.
Figure 6:
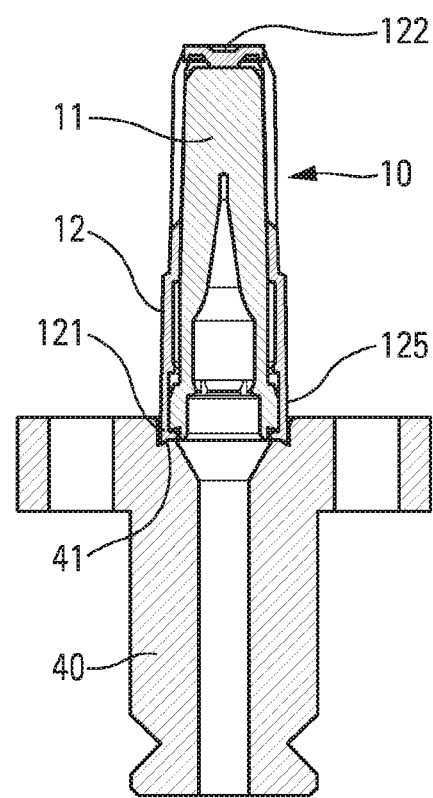
FIG. 6 is a view similar to the view in FIG. 5, during actuation of the shaper head.

In the description below, the terms "top" and "bottom" refer to the upright position of the rigid needle guard shown in the figures. The terms "axial" and "radial" refer to the longitudinal central axis A shown in FIG. 8.

The present invention applies to a rigid needle guard 10 comprising an inner part 11 made of elastomeric material, such as rubber or a TPE material, and a rigid outer body 12. Said rigid outer body 12 includes a bottom axial end and a top axial end surface 122. Said rigid outer body 12 is fastened to said inner part 11 made of elastomeric material via a folded-in portion 121 that is formed on the bottom axial end of said rigid outer body 12. Said folded-in portion 121 extends radially inwards from an outer peripheral surface 125 of said rigid outer body 12.

Said folded-in portion 121 is made, in known manner, by a folder head 30 that includes a folder cavity 31 of rounded shape that is adapted to deform said bottom axial end of said rigid outer body 12 so as to form a folded-in portion of rounded shape.

In the invention, the outer surface of said folded-in portion 121 forms, at its axially-bottom and radially-outer edge, a sharp and acute angle, preferably less than 90°, relative to the outer peripheral surface 125 of said rigid outer body 12.

The sharp and acute angle is formed by means of a shaper head 40 that modifies the rounded shape of said folded-in portion 121 formed by said folder head 30.

Folding by means of said folder head 30, which gives a rounded profile to said folded-in portion 121 so as to guarantee that said inner part 11 made of elastomeric material is fastened in said rigid outer body 12, is required, in particular so as to avoid any risk of crushing said outer body 12.

Thus, it is not desirable to modify the folder cavity 31 of the folder head 30 so as to give it a shape that defines a sharp and acute angle, since that would risk, during folding of the bottom axial end of said rigid outer body 12, deforming or crushing said rigid outer body 12, which could spoil said needle guard 10. Specifically, it is desirable, during the folding step, that the folded-in portion 121 extends radially inwards only, and that it does not form any radially-outward deformation on said outer peripheral surface 125 of said rigid outer body 12. In addition, it is desirable, during the folding step, that the folded-in portion 121 does not compress or deform said inner part 11 made of elastomeric material.

The invention thus envisages using the folder head 30 of the conventional assembly method and machine for forming a folded-in portion of rounded shape, and of adding thereto a shaper head 40 that acts after said folder head 30 so as to form said sharp and acute angle on said rounded folded-in portion.

Said shaper head 40 thus includes a shaper cavity 41 that defines a sharp and acute angle, the shaper cavity 41 coming to co-operate with said folded-in portion 121 so as to form, at its outer surface, a sharp and acute angle with the outer peripheral surface 125 of said rigid outer body 12.

Figure 7:
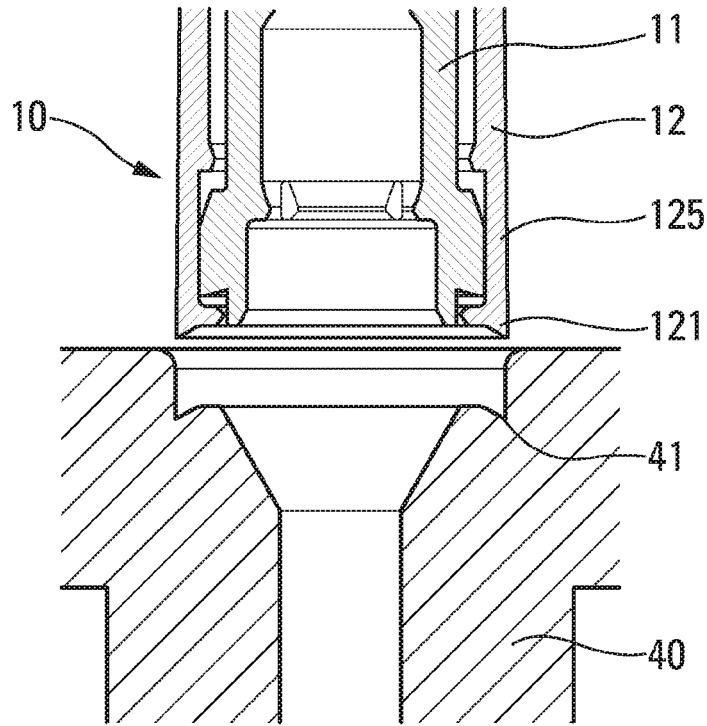
FIG. 7 is a view of a detail of FIG. 5, after actuating the shaper head.

The shape of said shaper cavity 41 shown in FIG. 7 is advantageous, but any other appropriate shape that makes it possible to generate a sharp and acute angle in the folded-in portion 121 at its axially-bottom and radially-outer edge could be envisaged.

Advantageously, said folder head 30 and said shaper head 40 operate hot, thereby making it easy to deform said folded-in portion 121 formed on the bottom axial end of said rigid outer body 12. In a variant, one or the other, or both of the folder and shaper heads 30, 40 could alternatively operate by ultrasound.

With the folded-in portion 121 shaped in accordance with the present invention with a sharp and acute angle, there is no longer any risk of a remover member 20, used for removing the rigid needle guard 10, e.g. in an autoinjector, sliding over said folded-in portion, as occurs with the rounded folded-in portion in FIG. 1.

Figure 8:
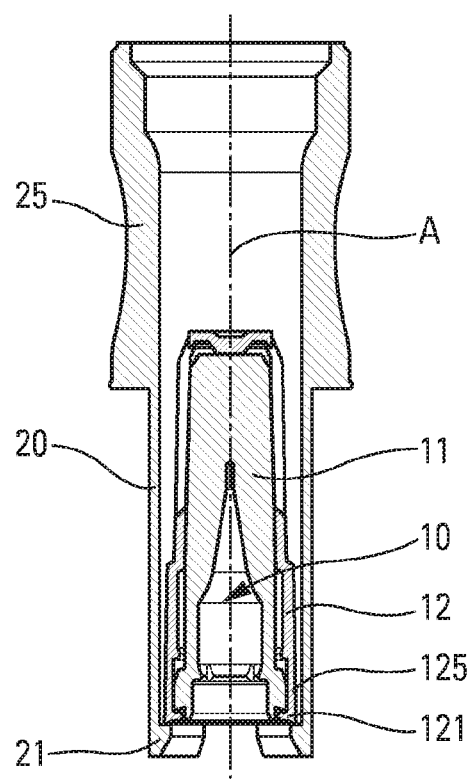
FIG. 8 is a diagrammatic section view of a rigid needle guard in an advantageous embodiment of the present invention, arranged in a remover member.

The remover member 20 includes a manual grip zone 25 on which the user places the fingers, so as to exert axial traction on the remover member. The remover member also includes a co-operation zone 21 for co-operating with said rigid needle guard 10, said co-operation zone 21 comprising at least one shoulder that extends radially inwards and that co-operates with said folded-in portion 121 of said rigid outer body 12 of said rigid needle guard 10. Thus, axial movement of said remover member 20 causes axial movement of said rigid needle guard 10. As can be seen in FIG. 8, as a result of the presence of the sharp and acute angle on the folded-in portion 121 of the invention, said at least one shoulder 21 of the remover member can no longer be disengaged from said folded-in portion 121, and removal of the rigid needle guard 10 is thus guaranteed with axial movement of the remover member 20.

Figure 9:
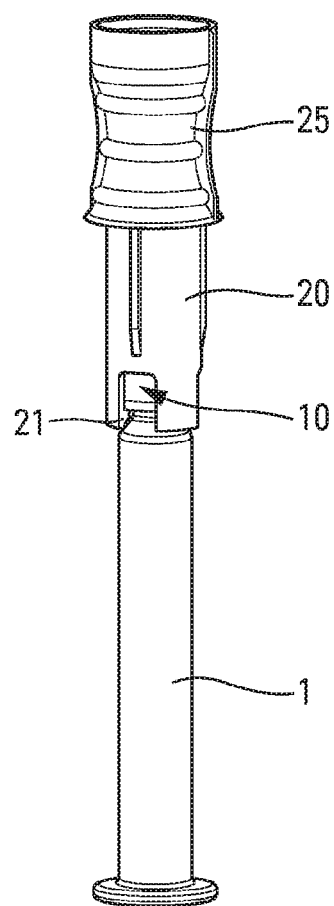
FIGS. 9 and 10 are diagrammatic views, respectively in perspective and in section, of the FIG. 8 unit, when assembled on a syringe provided with a needle.
Figure 10:
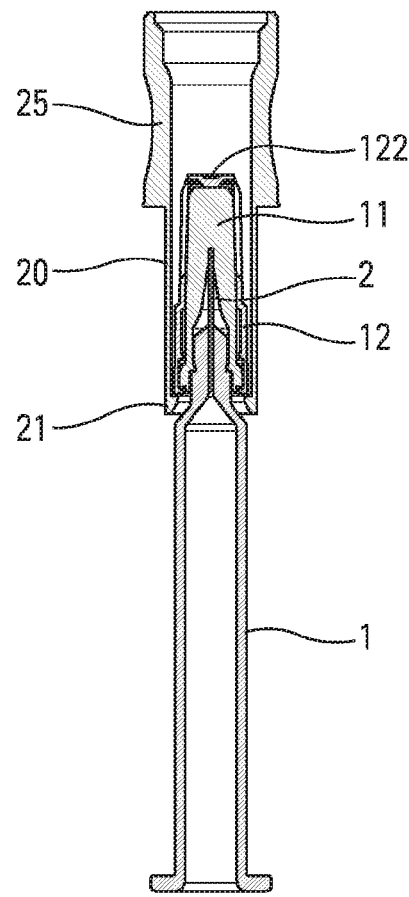

In FIGS. 9 and 10, a syringe comprising a reservoir 1 and a needle 2 is provided with a rigid needle guard 10 of the invention. Advantageously, said syringe is provided with a unit formed of such a rigid needle guard 10 and a remover member 20. Naturally, the syringe also includes a piston that is adapted to slide in the reservoir 1, a piston rod generally being provided so as to move said piston during injection. However, these elements and not shown in FIG. 10 since they do not form part of the present invention.

The present invention is described above with reference to a particular embodiment, but naturally it is not limited by said embodiment, but on the contrary, any useful modifications can be applied thereto by the person skilled in the art, without going beyond the ambit of the present invention, as defined by the accompanying claims.

The invention claimed is:

1. A rigid needle guard comprising an inner part made of elastomeric material, and a rigid outer body that is fastened to said inner part made of elastomeric material via a folded-in portion of a bottom axial end of said rigid outer body, said folded-in portion extending radially inwards from an outer peripheral surface of said rigid outer body, wherein the outer peripheral surface of said folded-in portion forms, at its axially-bottom and radially-outer edge, having a triangular shaped cross-section with an acute angle relative to the outer peripheral surface of said rigid outer body.

2. The rigid needle guard according to claim 1, wherein said sharp and acute angle is less than 90°.

3. The rigid needle guard according to claim 1, wherein said inner part made of elastomeric material is made of rubber or made of thermoplastic elastomer material.

4. A unit formed of a rigid needle guard and of a remover member that is arranged around said rigid needle guard, said rigid needle guard being made according to claim 1, wherein said remover member includes a grip zone and a co-operation zone for co-operating with said rigid needle guard, said co-operation zone comprising at least one shoulder that extends radially inwards and that co-operates with said axially-bottom and radially-outer edge of said folded-in portion of said rigid outer body of said rigid needle guard, such that axial movement of said remover member causes axial movement of said rigid needle guard.

5. A syringe comprising a reservoir and a needle, wherein said syringe includes a rigid needle guard according to claim 1.

6. An assembly method for assembling a rigid needle guard according to claim 1, the method comprising the following steps:
   inserting said inner part made of elastomeric material into said rigid outer body;
   folding the bottom axial end of said rigid outer body radially inwards by means of a folder head, so as to form a folded-in portion that fastens said inner part made of elastomeric material in said rigid outer body; and
   deforming said folded-in portion with a shaper head so as to shape, on said axially-bottom and radially-outer edge of said folded-in portion, a sharp and acute angle relative to the outer peripheral surface of said rigid outer body.

7. The method according to claim 6, wherein said step of folding the bottom axial end of said rigid outer body radially inwards is performed by heat or by ultrasound.

8. The method according to claim 6, wherein said step of deforming said folded-in portion is performed by heat or by ultrasound.

9. A rigid needle guard, comprising:
   an inner part made of elastomeric material and having an internal cavity configured to receive the rigid needle, the internal cavity having an insertion opening at a bottom end of the inner part and closed at an opposite top end of the internal cavity; and
   a rigid outer body having a top end and a bottom end, the bottom end of the rigid outer body is fastened to the inner part at the bottom end of the inner part via an inwardly extending portion of the bottom axial end of the rigid outer body;
   wherein the bottom end of the rigid outer body is a sharp outwardly protruding edge that, in a vertical cross-sectional plane, forms a triangular shape with an acute angle relative to an outer peripheral surface of the rigid outer body.

10. The rigid needle guard according to claim 9, wherein the sharp edge points axially downward in a direction away from the rigid outer body.

* * * * *